United States Patent [19]

Margosian et al.

[11] Patent Number: 5,423,315
[45] Date of Patent: Jun. 13, 1995

[54] MAGNETIC RESONANCE IMAGING SYSTEM WITH THIN CYLINDRICAL UNIFORM FIELD VOLUME AND MOVING SUBJECTS

[75] Inventors: Paul M. Margosian, Lakewood; Surya N. Mohapatra, Chesterland; James M. McNally, Chagrin Falls, all of Ohio

[73] Assignee: Picker International, Inc., Highland Hts., Ohio

[21] Appl. No.: 156,106

[22] Filed: Nov. 22, 1993

[51] Int. Cl.6 ............................................. A61B 5/055
[52] U.S. Cl. .............................. 128/653.2; 128/653.5; 324/309; 324/319; 324/321
[58] Field of Search ............... 128/653.2, 653.5, 653.1; 324/309, 319, 320, 318, 321

[56] References Cited

U.S. PATENT DOCUMENTS

| | | | |
|---|---|---|---|
| 4,829,252 | 5/1989 | Kaufman | 324/309 |
| 4,875,485 | 10/1989 | Matsutani | 128/653.5 |
| 4,981,136 | 1/1991 | Chance | 324/309 |
| 5,042,487 | 8/1991 | Marquardt | 128/653.5 |
| 5,154,178 | 10/1992 | Shah | 128/653.5 |
| 5,184,074 | 2/1993 | Kaufman et al. | 324/309 |
| 5,204,629 | 4/1993 | Ueyama et al. | 128/653.5 |
| 5,207,224 | 5/1993 | Dickinson et al. | 128/653.5 |
| 5,256,967 | 10/1993 | Foo et al. | 324/309 |
| 5,304,930 | 4/1994 | Crowley et al. | 324/309 |
| 5,305,749 | 4/1994 | Li et al. | 128/653.2 |

Primary Examiner—Krista M. Pfaffle
Attorney, Agent, or Firm—Fay, Sharpe, Beall, Fagan, Minnich & McKee

[57] ABSTRACT

A magnetic resonance gantry (A) includes a magnet (12) which generates a uniform magnetic field in a thin (under 15 cm thick) imaging volume (10). Gradient coils (30) and radio frequency coils (20) transmit radio frequency and gradient magnetic field pulses of conventional imaging sequences into the imaging volume. A patient support surface (42) moves a patient continuously through the imaging volume as the pulses of the magnetic resonance sequence are applied. A tachometer (52) monitors movement of the patient. A frequency scaler (54) scales the frequency of the RF excitation pulses applied by the transmitter (22) and the demodulation frequency of the receiver (26) in accordance with the patient movement such that the selected slice moves in synchrony with the patient through the imaging volume. The slice select gradient is indexed after magnetic resonance signals to generate a full set of views for reconstruction into a two-dimensional image representation of the slice are generated. The views for each slice are reconstructed (28) into a three-dimensional image representation that is stored in a memory (60). By using rapid imaging techniques, such as echo-planar techniques which can generate a two-dimensional image of a slice in 150 milliseconds, a three-dimensional diagnostic image of a section of a subject one meter long can be generated in less than 2 minutes.

25 Claims, 3 Drawing Sheets

MAGNETIC RESONANCE IMAGING SYSTEM WITH THIN CYLINDRICAL UNIFORM FIELD VOLUME AND MOVING SUBJECTS

BACKGROUND OF THE INVENTION

The present invention relates to the magnetic resonance arts. It finds particular application in conjunction with magnetic resonance diagnostic imaging and will be described with particular reference thereto.

In many medical diagnostic procedures, it is desirable or even necessary to generate an image representation of a relatively large volume of the subject. In prior art magnetic resonance imagers, the imaging volume is generally limited to a sphere within which the primary magnetic field is temporally invariant and uniform. Prior art magnetic resonance imaging systems typically have required a magnetic assembly with a patient receiving bore that is at least 1.5 meters long in order to provide a uniform imaging volume of about 40 cm in diameter. One disadvantage of these systems is that very large magnets and magnet assemblies are required. These very large magnet assemblies have several drawbacks including their large size, immense weight, and high cost. Not only are the magnets themselves expensive, but so are the large size related equipment for generating gradient magnetic fields, RF pulses, and the like.

Another disadvantage of the prior art magnetic resonance imagers is that they can only image a limited portion of the subject. Whole body scans are not impossible. Stretching the uniform magnetic field volume longitudinally adds significantly to the size and cost of the magnetic resonance scanner. Conducting several volume scans with the patient reposited between each one creates image registration problems.

One solution to these problems has been to use spiral CT scanners. Spiral CT scanners are not only much less expensive than conventional magnetic resonance equipment, but also enable the imaging volume to be greatly elongated. In addition to poor soft tissue contrast as compared to magnetic resonance imaging, spiral CT scanners have several other drawbacks. First, the data is collected along spirals which tends to skew the slices, introduce partial volume artifacts, and otherwise degrade the resultant image data. Further, magnetic resonance is preferable for distinguishing many types of tissue, particularly soft tissue and blood. Spiral CT scans to image the patient's circulatory system commonly require the infusion of a contrast agent into the blood. The contrast agent, which has good x-ray stopping power, is then imaged rather than the blood itself.

Another problem with spiral CT scanners resides in the heavy loading of the x-ray tube. Running the x-ray tube continuously for many slices places a great thermal load on the tube. Significant problems are encountered in removing excess thermal heat from the tube. Damage from unremoved excess thermal energy leads to premature x-ray tube failure or at least a very short x-ray tube life.

The present invention contemplates a new and improved magnetic resonance apparatus and method which enables a larger volume to be imaged with simpler, less-expensive equipment.

SUMMARY OF THE INVENTION

In accordance with one aspect of the present invention, a magnetic resonance apparatus is provided which creates a uniform magnetic field in a thin or cylindrical shaped volume. A patient support transports the subject through the volume during the magnetic resonance examination.

In accordance with preferred embodiment of the present invention, the uniform magnetic field volume is at least 45 cm in diameter and less than 15 cm thick, preferably less than 10 cm thick.

In accordance with a more limited aspect of the present invention, a slice selective RF frequency scaling means is provided for varying the RF frequency in accordance with patient movement through the uniform field volume. The frequency of the RF pulse is varied linearly as the patient is shifted along the uniform field volume such that the selected slice position remains constant with respect to the (moving) patient.

In accordance with another aspect of the present invention, the means for moving the subject includes a gantry which itself is movable.

In accordance with another aspect of the present invention, a moving means is provided for moving the magnet and associated hardware for generating the uniform field volume.

In accordance with another more limited aspect of the present invention, the moving means enables the magnet and associated structure to be moved to different locations.

In accordance with another more limited aspect of the present invention, the moving means enables an orientation of the imaging volume disk to be reoriented, e.g. horizontally. Means are provided for causing relative movement between a patient standing vertically and the magnet and associated hardware assembly.

In accordance with another aspect of the present invention, a method of magnetic resonance imaging is provided. A uniform temporally constant magnetic field is created in a thin imaging volume which is at least twice a slice thickness and less than 15 cm thick. A patient is moved longitudinally and continuously through the thin imaging volume. Images from a plurality of slices are generated sequentially as the patient moves to create a volume image representation.

In accordance with a more limited aspect of the present invention, a single projection or one-dimensional image is taken along each slice. The one-dimensional images are assembled into a projection or shadowgraphic image, analogous to a conventional photographic film shadowgraphic x-ray image.

In accordance with another aspect of the present invention, views for a two-dimensional image representation are collected for each slice and the views are reconstructed using Fourier transform reconstruction techniques.

In accordance with a more limited aspect of the present invention, the views are generated using echo-planar imaging techniques.

In accordance with another aspect of the present invention, the patient's blood is imaged to generate contrast and flow rate information.

In accordance with another aspect of the present invention, a centric phase encoding scheme is utilized. High frequency phase encoding components are collected more closely in time than centrally phase encoded views.

In accordance with another aspect of the present invention, centrally phase encoded views are shared between contiguous slices.

In accordance with another aspect of the present invention, a slice select gradient is scaled in coordination with the continuous patient movement to enable the patient to be moved more quickly without image degradation.

One advantage of the present invention resides in its low cost.

Another advantage of the present invention resides in its reduced physical size and weight.

Another advantage of the present invention is that it enables volumes of indefinite length to be imaged.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
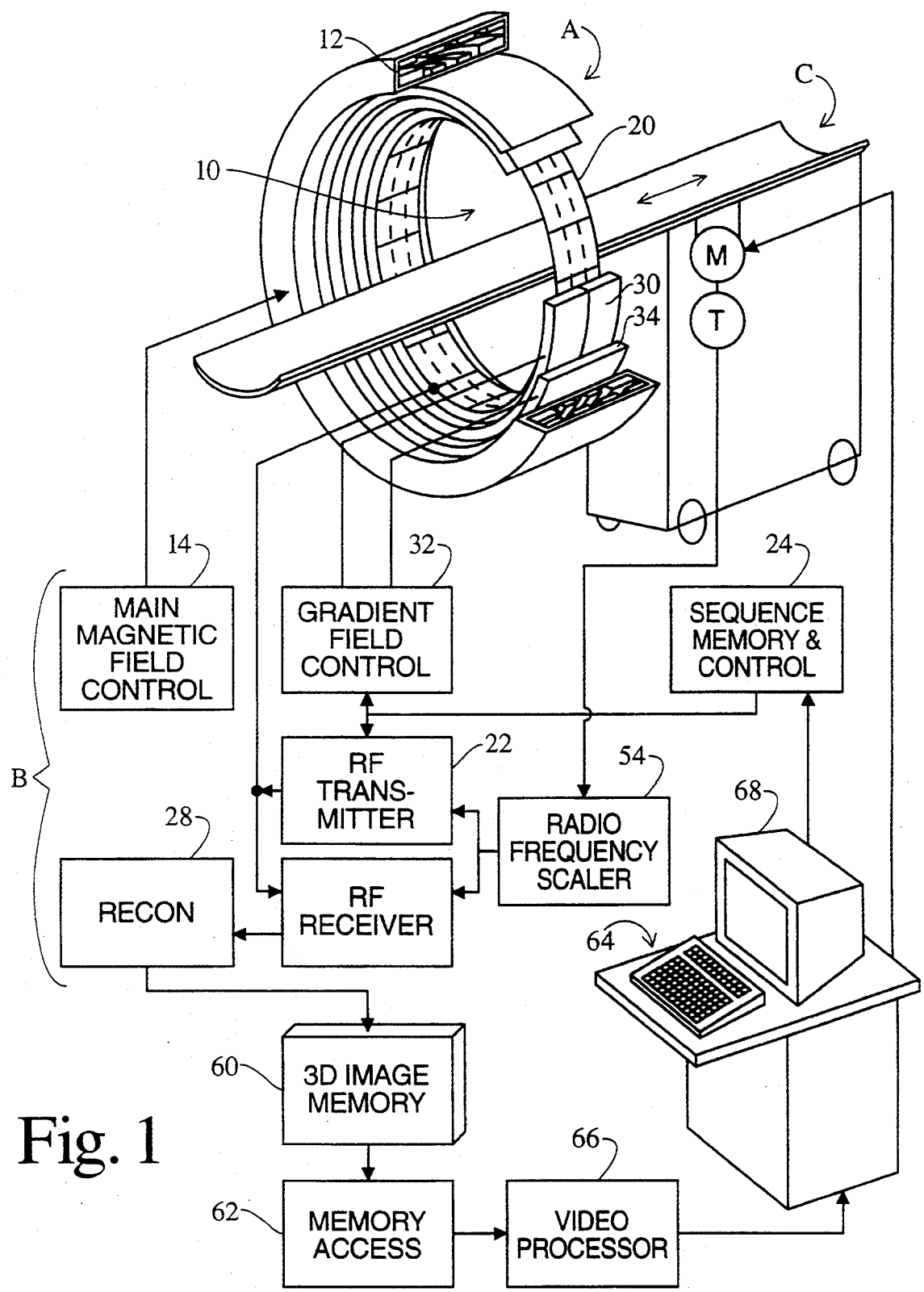
FIG. 1 is a diagrammatic illustration of a magnetic resonance imaging system in accordance with the present invention.

With reference to FIG. 1, a gantry A is operated by an electronic processing and control circuit B to excite and manipulate magnetic resonance in a thin imaging volume 10 that is only 2-20 slices thick. The processing and control circuit processes resultant resonance signals from the imaging volume into image representations. A patient transport assembly C moves a patient through the imaging volume during the imaging process.

A main magnet assembly 12, preferably a self-shielded superconducting magnet assembly, generates a primary magnetic field which is temporally constant and uniform in the thin imaging volume 10. In the preferred embodiment, the imaging volume 10 is a thin disk, about 45 cm or more in diameter, transverse to the longitudinal direction. Preferably, the thin volume 10 is sufficiently wide that about 10-20 parallel slices can be generated within the imaging volume 10. This enables the scanner to be used for brain scans and obtain traditional volume image representations representing about a 15 cm thick slab through the brain without moving the patient. However, it is to be appreciated, that an imaging volume 10 which is twice the thickness of the maximum available slice is satisfactory. A width of two slices is sufficient to image an indefinite length of the patient when the patient is being moved continuously through the examination region. A main magnetic field control means 14 controls the main magnet assembly 12. For a superconducting magnet assembly, the magnetic field control 14 is used to ramp up the magnetic field. For a resistive main magnet, the main magnetic field control 14 not only turns on and turns off the main magnet, but also maintains a uniform current flow.

A radio frequency coil 20 surrounds the imaging volume 10. The RF coil is preferably relatively narrow in the longitudinal direction and shaped for (1) transmitting magnetic field signals substantially exclusively into the imaging volume 10 and (2) receiving radio frequency signals substantially exclusively from the imaging volume. Preferably, a radio frequency shield surrounds the RF coil 20 to prevent radio frequency signals from being irradiated radially outward and to render the radio frequency coil more insensitive to radio frequency signals from outside the imaging volume. A radio frequency transmitter 22 selectively supplies radio frequency current pulses to the radio frequency coil to cause radio frequency pulses to be transmitted into the volume region for exciting and manipulating magnetic resonance. A magnetic resonance imaging sequence memory and control 24 controls the radio frequency transmitter 22 to control the timing and amplitude of the radio frequency pulses to implement any one of a large plurality of conventional magnetic resonance imaging or spectroscopy sequences. A radio frequency receiver 26 is also connected with the radio frequency coil for demodulating radio frequency signals, particularly magnetic resonance signals from within the imaging volume 10 to generate a plurality of magnetic resonance views corresponding to each imaged slice. A reconstruction processor 28 reconstructs the views corresponding to each slice into a two-dimensional image representation. Alternately, each view can be a projection at a different angle which are reconstructed with a projection, CT-type algorithm. When the patient is moving at a constant speed, as discussed below, a conventional spiral CT reconstruction scheme is used.

A gradient coil assembly 30 operates under control of a gradient field control means 32 to generate magnetic field gradients in the imaging volume. More specifically, the gradient field control 32 supplies current to the gradient coils 3e to cause magnetic field gradients along the longitudinal axis (slice select gradients) and along mutually orthogonal axes transverse to the longitudinal direction (read and phase encode gradients). The magnetic resonance imaging sequence memory and control 24 causes the gradient control 32 and the radio frequency transmitter 22 to apply coordinated radio frequency and gradient pulses of conventional sequences such that resonance is limited to a selected slice orthogonal to the longitudinal direction for each view. Active gradient shield coils 34 are disposed around the gradient coils 30 to limit the gradient magnetic field substantially to the imaging volume 12.

A patient transport means C includes a gantry 40 that supports a patient or other subject within the examination region. The patient gantry 40 includes a patient supporting surface 42 and a motor and gear assembly 44 for continuously moving the patient supporting surface 42 longitudinally through the imaging volume at a selectable velocity. It is to be appreciated, that the continuous longitudinal movement of the patient will cause each view from the radio frequency receiver 26 to represent a slightly shifted slice if the slice select gradient remains constant in each repeat of the imaging sequence. If the patient is moved sufficiently slowly, preferably less than $\frac{3}{4}$ of a slice width before all views of an image are collected, satisfactory images can be obtained nonetheless.

Figure 2:
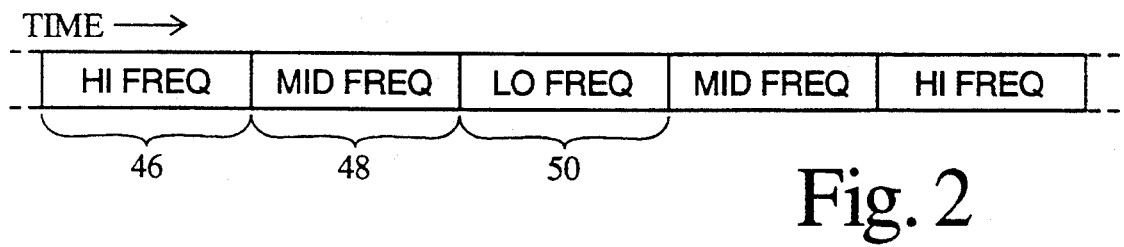
FIG. 2 is a diagrammatic illustration of a centric phase encoding scheme in accordance with the present invention.

With reference to FIG. 2, motion artifacts due to the moving patient tend to be highly pronounced in the views with the highest frequency phase encoding. Accordingly, the high frequency phase encoding views in both the positive and negative direction are collected contiguously in a high frequency view region Progressively lower frequency views are taken contiguous to the immediately preceding and following high frequency views in temporal regions 48. The low frequency views 50 are furthest displaced from the high frequency views. As illustrated in FIG. 2, the lowest or central-most views are taken at the beginning and end of the scan. In a 128 view image set in which the highest positive phase encode frequency view is 1, the highest negative phase encode frequency view is 128, and the central or zero phase encode view is 64, a suitable view order is: 1, 128, 2, 127, 3, 126, . . .

In one alternate embodiment, the low frequency or central views are shared by contiguous slices for greater processing efficiency.

Preferably, the frequency of the RF excitation and refocusing is scaled in coordination with movement of the patient such that the position of the selected slice remains constant with respect to the moving patient for all views even as the selected slice shifts axially through the imaging volume. To this end, a patient motion and sequence timing coordinating means, such as a tachometer 52 is connected with the patient support moving assembly 44 to provide signals indicative of movement of the selected slice through the imaging volume. A frequency scaling means 54 adjusts the RF amplifier 22 such that the RF excitation frequency and the RF demodulation frequency vary slightly with each view when the subject is moving through the imaging volume. The effect of this is to move the selected slice with the moving patient, so that it is fixed relative to the patient. Alternatively, the clock of the sequence memory and control 24 may control the motor 44 such that the patient support 42 is controlled to move in coordination with the imaging sequence.

In one embodiment, the images are rendered insensitive to variations in blood flow during the cardiac cycle by recording the cardiac waveform (from EKG) and analyzing it in a computer to calculate patient support movement speed such that the patient moves one slice thickness per integer number of heartbeats (typically one or two). Preferably, the clock of the sequence memory and control 24 is adjusted to control the sequence timing and the motor 44 to move the patient support 42 at the calculated speed. RF frequency is scaled linearly with time during the acquisition to fix the selected slice to the moving patient, as described in the previous paragraph. By this means, synchronization of acquisition and slice position with both the cardiac cycle and the movement of the patient support is accomplished.

As the two-dimensional image of each slice is reconstructed with either Fourier or projection reconstruction algorithms, it is stored in a three-dimensional, image memory 60. This creates a three-dimensional, image representation in which the z-axis resolution is determined by the speed of patient transport, the thickness of the image slice, and the duration required to collect the views for reconstructing each two-dimensional image representation. The x and y-axis resolutions are determined by the number of differently phase encoded views and the frequency resolution. The voxels are rectangular prisms that may have different dimensions along all three axes. A memory access means 62 under control of an operator control panel 64 selectively accesses the voxel values of the three-dimensional image memory 60 to retrieve selected two-dimensional image representations. Transverse, sagittal, coronal, oblique, 3D, and other image representations, as are conventional in the art, are retrieved from the three-dimensional image memory 60 and converted by a video processor 66 into appropriate format for display on a video monitor 68. The operator also uses the operator control panel 64 for selecting among the multiplicity of available imaging sequences and imaging sequence parameters (repeat time, number of phase encode steps, etc.) which the magnetic resonance imaging sequence memory and control 24 implements. The operator control panel is further used for controlling the patient moving assembly 44 for controlling the speed with which the patient is moved through the examination volume For greater patient processing efficiency, the gantry 40 preferably has wheels 70 or the like which enable it to be moved. This enables the subject to be moved between the disclosed magnetic resonance apparatus and other diagnostic scanners, such as CT, SPECT, ultrasound, or the like. This portability further enables one patient to be prepared on one gantry in a preparation room while another patient is undergoing examination on another gantry.

Various types of diagnostic imaging procedures can advantageously be performed with this system. For example, the apparatus can be run in a shadowgraphic survey mode in which the equivalent of a shadowgraphic film x-ray is taken in a plane parallel to the patient support surface 42. The patient is moved continuously and rapidly through the imaging volume. For each slice, a view is generated with no phase encoding but which is frequency encoded with a frequency encode or read gradient in a horizontal direction. The "image" for each slice is a one-dimensional image which represents the projection in a vertical direction. When the one-dimensional images for the slices along the entire length of the patient are assembled, a two-dimensional projection image analogous to a shadowgraphic film x-ray is generated. Such a projection survey image is advantageously used to identify regions of the patient for further imaging and study, further positioning of the patient, contrast adjustments, and the like.

As another option, a two-dimensional image representation is generated for each slice using an echo-planar imaging technique which enables each two-dimensional slice image to be generated in about 150 milliseconds. The time to generate each two-dimensional image will, of course, vary with the resolution of the resultant image. However, in a relatively coarse mode (relatively few views per image), eight two-dimensional slice images can be generated per second. This enables an image to be generated in substantially real time. Such images are potentially valuable for magnetic resonance fluoroscopy and other applications.

In another application, flow imaging techniques are utilized. That is, a conventional magnetic resonance sequence is selected which causes the value of each pixel of the slice image to vary with the velocity of the corresponding tissue. In this manner, an image is generated in which gray scale, color, or the like is indicative not of tissue type, but of tissue velocity. Imaging sequences designed for imaging blood can be used concurrently such that images depicting both blood and blood flow velocity of an imaged volume are generated.

This technique can be used to measure blood flow through various regions of the body, e.g. the legs for measuring thrombosis. The technique can also be used for measuring or monitoring the patient's cardiac cycle. A traditional EKG measures each time the heart beats, but does not indicate whether or how much blood was pumped with each cycle. The present technique can be utilized to measure the fluid actually pumped by the heart in each beat.

The rapid imaging time, particularly when using echo-planar imaging sequences, is ideally suited for motion studies. Because the imaging volume 10 is so thin, the volume within which the uniform field is created is relatively small. The imaging bore can be larger in diameter than today's conventional magnetic resonance imaging equipment while still effecting a significant decrease in the size and power consumption of the magnet 12 and the other described hardware. A larger bore enables the patient to move an imaged joint without interference from the bore of the imager. Free patient movement is also facilitated by the relatively short axial dimension of the bore. The combination of space for patient movement and rapid imaging, particularly with echo-planar techniques, is ideal for generating a series of volume images of an examined joint as the joint is flexed.

This system is also advantageous in shock and trauma examinations. When a patient is suffering from shock, the physician only has about 3 minutes to work. By using a relatively coarse pixel resolution, a three-dimensional scan of the entire patient can be made in under 3 minutes. This rapid scan technique is also advantageous for rapid screenings for preselected conditions. For example, a magnetic resonance imaging sequence and parameters are selected which are particularly sensitive to a selected condition such as tuberculosis, a selected type of cancer, or the like, and the rapid survey technique is run to locate any regions of the body which require further examination. Because such survey scans can be run in under 3 minutes, the technique finds utility for screening large numbers of people for a specific condition.

Figure 3:
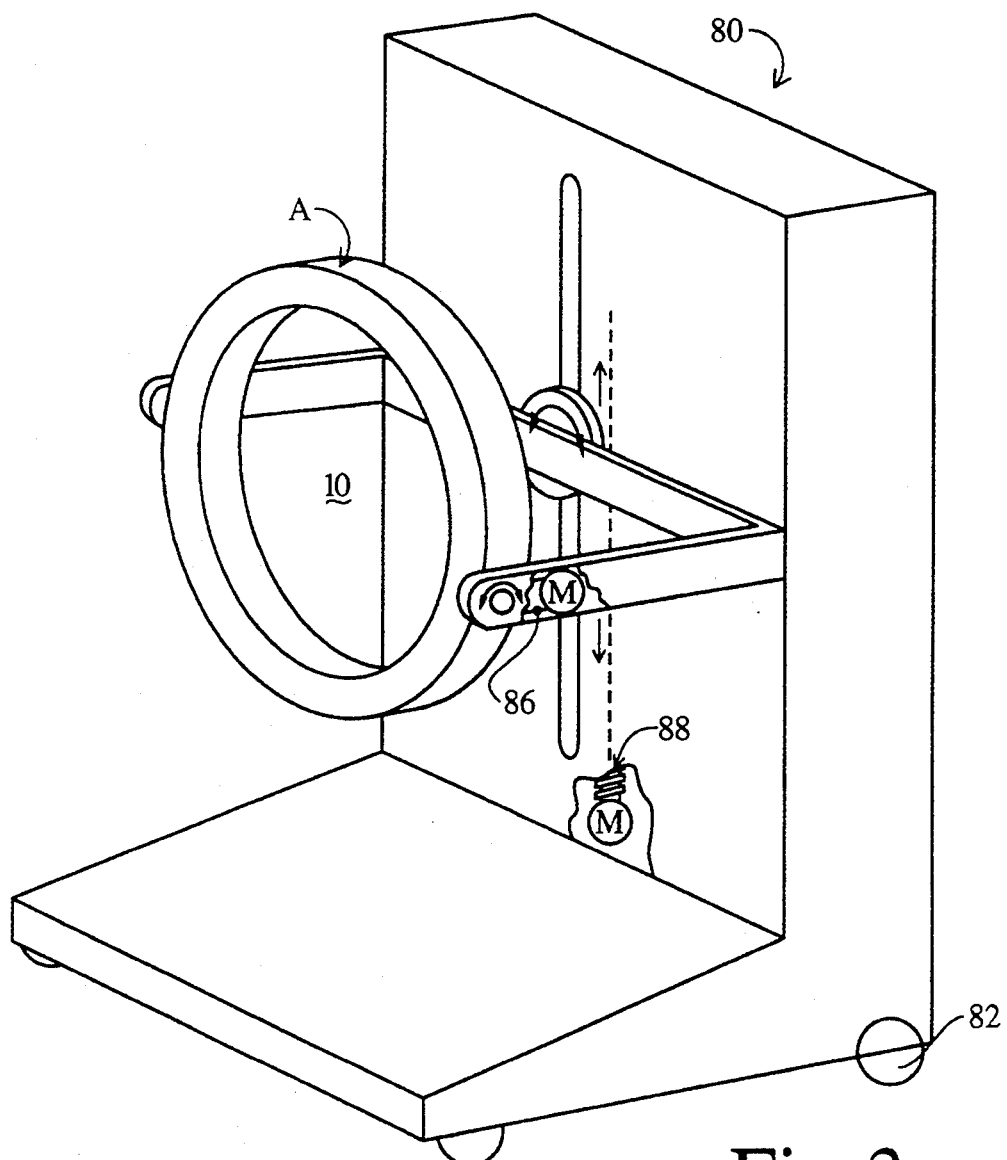
FIG. 3 is a diagrammatic illustration of a portable magnetic resonance imaging apparatus in accordance with the present invention; and, FIG. 4 is an alternate embodiment of the present invention which uses a permanent magnet to provide a thin rectangular imaging volume.

With reference to FIG. 3, the gantry assembly A including the main magnet, gradient, and radio frequency coils, is mounted to a gantry 80 for selectively moving the imaging volume 10. More specifically, the gantry 80 includes wheels 82 or the like which enable the entire assembly to be transported to other locations.

The gantry 80 further includes a means 86 for changing the angular orientation of the thin imaging volume 10. In the illustrated embodiment, the gantry A is pivotally mounted to support arms which carry a motor and gear box assembly for driving the gantry A to rotate. Preferably, this enables the gantry to be positioned with the imaging volume in a horizontal plane. A means 88 is provided for causing relative vertical movement between the imaging volume 10 and a standing patient. In the illustrated embodiment, the means 88 includes a drive screw and motor for moving the gantry supporting arms vertically. However, an elevator assembly for raising and lowering the standing patient are also contemplated.

Figure 4:
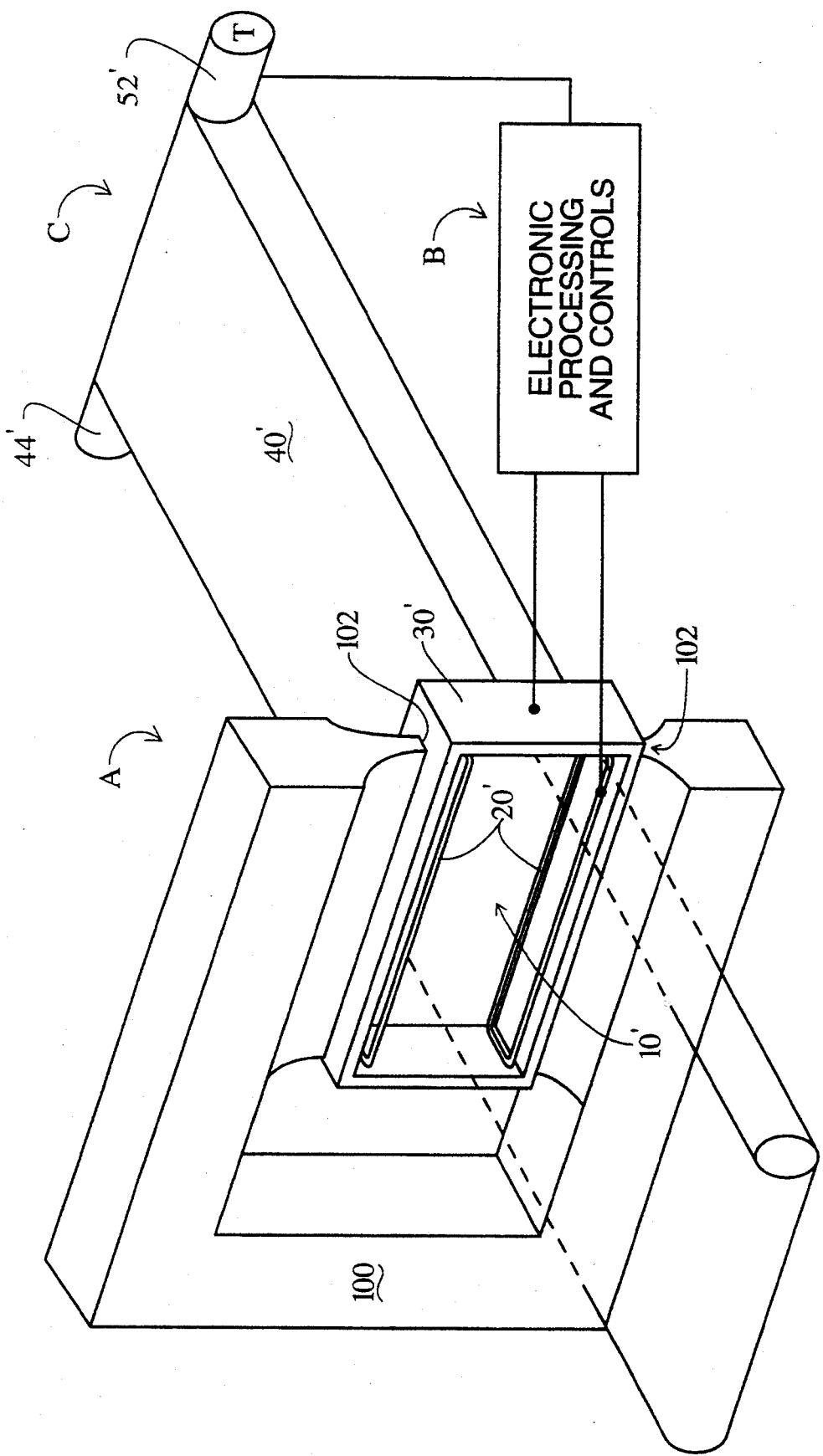

With reference to FIG. 4, the present invention is also applicable to permanent magnet systems. The gantry assembly A includes a permanent, horseshoe-shaped magnet 100 which has pole faces 102 disposed on opposite sides of a thin, generally rectangular imaging volume 10'. Gradient coils 30' surround the imaging volume for selectively causing magnetic field gradients thereacross. Radio frequency coils 20' are disposed adjacent the imaging volume for transmitting radio frequency pulses into and receiving radio frequency magnetic resonance signals from the imaging volume 10'. A patient support and transporting means C is driven by a motor assembly 44' to move the subject longitudinally through the imaging volume 10' with controlled continuous movement. A tachometer 52' measures the patient velocity and provides such patient velocity signals to the electronic control and imaging means B to shift the selected slice in the coordinate system of the gantry in accordance with patient movement such that the slice remains fixed in the coordinate system of the patient.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A magnetic resonance apparatus comprising:
  a patient receiving sleeve;
  a thin main field magnet disposed around the patient receiving sleeve defining a thin imaging volume having a height, a width, and a thickness, which imaging volume thickness is (i) at least twice a slice thickness, (ii) less than 15 cm thick, and (iii) smaller than the imaging volume height and width; said magnet generating a main magnetic field which is uniform and temporally constant within said thin imaging volume which is transverse to a central axis of the patient receiving sleeve, which thin imaging volume is thin in a direction parallel to the axis of the patient receiving sleeve;
  a radio frequency coil disposed around the thin imaging volume;
  a patient support and transport means for supporting a patient and moving the patient axially, transverse to and through the thin imaging volume during a magnetic resonance examination.

2. The apparatus as set forth in claim 1 further including a gradient coil assembly disposed around the radio frequency coil for creating gradient magnetic fields along orthogonal directions in the thin imaging volume.

3. The apparatus as set forth in claim 2 further including:
  a magnetic resonance imaging sequence memory and control means for designating magnetic field gradient and radio frequency pulses of a selected magnetic resonance imaging sequence;
  a radio frequency transmitter connected with the sequence memory and control means and the radio frequency coil for transmitting the designated radio frequency pulses into the thin imaging volume;
  a gradient field control means connected with the sequence memory and control means and the gradient coil assembly for causing the gradient coil assembly to create the gradient magnetic fields in the thin imaging volume;
  a radio frequency receiver for receiving radio frequency signals from the thin imaging volume and demodulating the received signals into electronic views;

a reconstruction means for reconstructing the views into a three-dimensional image representation;

an image memory for storing the three-dimensional image representation.

4. The apparatus as set forth in claim 1 further including an thin imaging volume locating means for moving the patient receiving sleeve, the main field magnet, and the radio frequency coil for relocating the thin imaging volume.

5. The apparatus as set forth in claim 1 wherein the patient support and transport means includes a patient supporting surface, a carriage, and a plurality of wheels such that the patient supporting surface and carriage can be wheeled from place to place, whereby one patient can be prepared for the examination in a remote location while another patient is being examined and whereby the patient can be moved without repreparation from one diagnostic apparatus to another.

6. The apparatus as set forth in claim 1 wherein the main field magnet includes a permanent magnet having oppositely disposed pole faces of substantially the width of the thin imaging volume such that the thin imaging volume is defined therebetween.

7. A magnetic resonance apparatus comprising:
a patient receiving sleeve;
a main field magnet disposed around the patient receiving sleeve for generating a temporally constant main magnetic field within an examination volume which is thin in a direction parallel to the axis of the patient receiving sleeve;
a radio frequency coil disposed around the examination volume;
a patient support and transport means for supporting a patient and moving the patient axially through the examination volume during a magnetic resonance examination; and
a means for shifting an image slice relative to a coordinate system of the main field magnet in coordination with movement of the patient by the patient support and transport means.

8. The apparatus as set forth in claim 7 further including active gradient shield coils disposed around the gradient coil assembly, the gradient coil assembly and the active gradient shield coil assembly acting together to (1) create the magnetic field gradients in the examination volume and (2) to cancel magnetic field gradients outside of the examination volume.

9. A magnetic resonance imaging apparatus comprising:
a patient receiving sleeve;
a main field magnet disposed around the patient receiving sleeve for generating a main magnetic field with is temporally constant within an examination volume which is thin in a direction parallel to the axis of the patient receiving sleeve;
a radio frequency coil disposed around the examination volume;
a gradient coil assembly disposed around the radio frequency coil for creating gradient magnetic fields along the orthogonal directions in the examination volume;
a patient support and transport for supporting a patient and moving the patient axially through the examination volume during a magnetic resonance examination;
a magnetic resonance imaging sequence memory and control for designating magnetic field gradient and radio frequency pulses of a selected magnetic resonance imaging sequence;

a gradient field control connected with the sequence memory and control and the gradient coil assembly for causing the gradient coil assembly to create the gradient magnetic fields in the examination volume, the gradient field control causing the gradient coils to apply at least slice select gradients along the patient receiving sleeve axis;

a radio frequency receiver for receiving radio frequency signals from the examination volume and demodulating the received signals into electronic views;

a radio frequency scaling control connected with the radio frequency transmitter and the radio frequency receiver for incrementing resonance frequency in accordance with movement of the patient support and transport means;

a reconstruction processor for reconstructing the views into a three-dimensional image representation;

an image memory for storing the three-dimensional image representation.

10. The apparatus as set forth in claim 9 wherein the reconstruction processor uses a Fourier transform reconstruction technique to reconstruct a plurality of phase-encoded views corresponding to a single slice of an examined subject into a two-dimensional image representation, the sequence memory and control causing the gradient field control to index the slice select gradient to a next adjacent slice after the views for each slice have been generated, such that the three-dimensional image representation includes a series of parallel two-dimensional image representations.

11. The apparatus as set forth in claim 9 wherein the a reconstruction processor performs a projection transform reconstruction procedure to reconstruct a plurality of angularly displaced projection views corresponding to a single slice of an examined subject into a two-dimensional image representation, the sequence memory and control causing the gradient field control to index the slice select gradient to a next adjacent slice after the views for each slice have been generated, such that the three-dimensional image representation includes a series of parallel two-dimensional image representations.

12. A magnetic resonance imaging apparatus comprising:
a patient receiving sleeve;
a main field magnet disposed around the patient receiving sleeve for generating a main magnetic field which is uniform and temporally constant within an examination volume which is thin in a direction parallel to the axis of the patient receiving sleeve;
a radio frequency coil disposed around the examination region;
a gradient coil assembly disposed around the examination volume for creating gradient magnetic fields along orthogonal directions in the examination volume;
a patent support and transport for supporting a patient and moving the patient axially through the examination volume during a magnetic resonance examination;
a magnetic resonance imaging sequence memory and control for designating magnetic field gradient and radio frequency pulses of a selected magnetic resonance imaging sequence;

a radio frequency transmitter connected with the sequence control and the radio frequency coil for transmitting the designated radio frequency pulses into the examination volume;

a gradient field control connected with the sequence control and the gradient coil assembly for causing the gradient coil assembly to create the gradient magnetic fields in the examination volume;

a radio frequency receiver for receiving radio frequency signals from the examination volume and demodulating the received signals into electronic views;

a reconstruction processor which performs a Fourier transform reconstruction on a plurality of the views corresponding to a single slice of an examined subject into a two-dimensional image representation, the imaging sequence control causing the gradient field control to index the slice select gradient to a next adjacent slice after the views for each slice have been generated, such that a series of parallel two-dimensional image representations are generated.

13. A magnetic resonance imaging apparatus comprising:

a cylindrical patient receiving sleeve;

a main field magnet disposed around the patient receiving sleeve for generating a main magnetic field is uniform and temporally constant is a cylindrical examination volume at least 45 cm in diameter and less than 15 cm thick in a direction parallel to the axis of the patient receiving sleeve;

a gradient coil assembly disposed around the radio frequency coil for creating gradient magnetic fields along orthogonal directions in the examination volume;

a radio frequency coil disposed around the examination volume;

a patient support and transport for supporting a patient and moving the patient axially through the examination volume during a magnetic resonance examination;

a magnetic resonance imaging sequence control for designating magnetic field gradient and radio frequency pulses of a selected magnetic resonance imaging sequence;

a radio frequency transmitter connected with the sequence control and the radio frequency coil for transmitting the designated radio frequency pulses into the examination volume;

a gradient field control connected with the sequence control and the gradient coil assembly for causing the gradient coil assembly to create the gradient magnetic fields in the examination volume;

a radio frequency receiver for receiving radio frequency signals from the examination volume and demodulating the received signals into electronic views;

a reconstruction processor for reconstructing the views into a three-dimensional image representation;

an image memory for storing the three-dimensional image representation.

14. A magnetic resonance apparatus comprising:

a patient receiving sleeve;

a main field magnet disposed around the patient receiving sleeve for generating a main magnetic field which is uniform and temporally constant within an examination volume which is thin in a direction parallel to the axis of the patient receiving sleeve;

a radio frequency coil disposed around the examination volume;

a rotating means for rotating the patient receiving sleeve, the main field magnet, and the radio frequency coil such that the examination volume is disposed in a substantially horizontal plane; and a means for moving a standing patient and the examination volume relative to each other along a vertical axis.

15. A method of magnetic resonance imaging comprising:

creating a uniform, temporally constant magnetic field in a thin imaging volume which has a height, a width, and a thickness which imaging volume thickness is (i) at least twice a slice thickness, (ii) less than 15 cm thick, and (iii) smaller than the imaging volume height and width;

moving a subject continuously through the thin imaging volume transverse to the imaging region height and width;

while the subject is moving through the thin imaging volume, exciting and manipulating magnetic resonance in a selected slice of the subject that is in the imaging region and receiving magnetic resonance signals from the selected slice;

reconstructing the magnetic resonance signals from a plurality of slices into an image representation.

16. The method as set forth in claim 15 wherein the step of exciting and manipulating magnetic resonance and receiving magnetic resonance signals from the selected slice includes applying a slice select gradient along a direction of subject movement and further including:

shifting the selected slice relative to the imaging volume such that the selected slice remains fixed relative to the subject.

17. The method as set forth in claim 16 further including after receiving a full set of magnetic resonance signals from the selected slice for reconstruction into a two-dimensional slice image, indexing the slice select gradient to select a next adjacent slice of the subject and repeating the exciting and manipulating magnetic resonance and receiving magnetic resonance signal step and the shifting step.

18. The method as set forth in claim 17 wherein the reconstructing step includes at least one of Fourier transform reconstructing and projection reconstruction of the magnetic resonance signals into a plurality of parallel two-dimensional slice images.

19. The method as set forth in claim 16 wherein the magnetic resonance exciting and manipulating includes applying an echo-planar imaging sequence.

20. The method as set forth in claim 19 wherein the echo-planar imaging sequence is applied with a repeat time and a resolution such that two-dimensional images of at least six slices are generated per second, whereby substantially real time imaging is provided.

21. The method as set forth in claim 15 wherein a single one-dimensional projection image of each slice is obtained, the one-dimensional projection images of a multiplicity of slices taken together being a two-dimensional shadowgraphic, projection image.

22. A method of magnetic resonance imaging comprising:

creating a temporally constant magnetic field in an imaging region which is at least twice a slice thickness and less than 15 cm thick;

moving a subject continuously through the thin imaging volume;

while the subject is moving through the thin imaging volume, exciting and manipulating magnetic resonance in a selected slice of the subject that is in the imaging volume and receiving magnetic resonance signals from the selected slice, the step of exciting and manipulating magnetic resonance and receiving magnetic resonance signals from the selected slice including:

applying a slice select gradient along a direction of subject movement, and incrementing a frequency of the excited resonance and a demodulation frequency of the received resonance signals to shift the selected slice;

reconstruction the magnetic resonance signals from a plurality of slices into an image representation.

23. The method as set forth in claim 22 further including:

monitoring a cardiac cycle of the subject;

coordinating moving of the subject and incrementing of the frequency of the excited resonance and the demodulation frequency with the monitored cardiac cycle.

24. A method of magnetic resonance imaging comprising:

creating a uniform, temporally constant magnetic field in an imaging volume which is at least twice a slice thickness and less than 10 cm thick;

moving a subject continuously through the thin imaging volume;

while the subject is moving through the thin imaging volume, exciting and manipulating magnetic resonance in a selected slice of the subject that is in the imaging region, the magnetic resonance exciting and manipulating including:

applying a slice select gradient along a direction of subject movement, applying phase encode gradients which are changed in each repetition such that the received magnetic resonance signals have a range of phase encoding from a central phase encoding to positive and negative high frequency phase encodings on opposite sides of the central phase encoding, applying the positive and negative high frequency phase encoding gradients in temporally contiguously repetitions and applying the central phase encoding gradient in less temporally contiguous repetitions;

receiving magnetic resonance signals from the selected slice;

after receiving a full set of magnetic resonance signals from the selected slice for reconstruction into a two-dimensional slice image, indexing the slice select gradient to select a next adjacent slice of the subject and repeating the exciting and manipulating of magnetic resonance and the receiving magnetic resonance signals;

reconstructing the magnetic resonance signals from a plurality of slices into an image representation.

25. A method of magnetic resonance imaging comprising:

creating a uniform, temporally constant magnetic field in an imaging region which is at least twice a slice thickness and less than 15 cm thick;

moving a subject continuously through the thin imaging region, while the subject is moving through the thin imaging region, exciting and manipulating magnetic resonance in a selected slice of the subject that is in the imaging region including:

applying a slice select gradient along a direction of subject movement, shifting the selected slice relative to the imaging region such that the selected slice remains fixed relative to the subject, applying a flow imaging magnetic resonance sequence such that the reconstructed image representation represents flow velocities;

receiving magnetic resonance signals from the selected slice;

reconstructing the magnetic resonance signals from a plurality of slices into an image representation.

* * * * *